United States Patent [19]
Foguet et al.

[11] Patent Number: 5,665,736
[45] Date of Patent: Sep. 9, 1997

[54] N-BENZOYLMETHYL-PIPERIDINES

[75] Inventors: Rafael Foguet; Santiago Gubert; Aurelio Sacristan; José A. Ortiz, all of Barcelona, Spain

[73] Assignee: Ferrer Internacional, S.A., Barcelona, Spain

[21] Appl. No.: 557,008

[22] PCT Filed: Mar. 17, 1995

[86] PCT No.: PCT/EP95/01007

§ 371 Date: Feb. 20, 1996

§ 102(e) Date: Feb. 20, 1996

[87] PCT Pub. No.: WO95/25732

PCT Pub. Date: Sep. 28, 1995

[30] Foreign Application Priority Data

Mar. 18, 1995 [ES] Spain ............... 9400582

[51] Int. Cl.[6] ............... A61K 31/445; C07D 405/12
[52] U.S. Cl. ............... 514/321; 546/197
[58] Field of Search ............... 514/321; 546/197

[56] References Cited

U.S. PATENT DOCUMENTS 4,721,723 1/1988 Barnes ............... 514/321
5,158,961 10/1992 Jakobsen et al. ............... 514/321

OTHER PUBLICATIONS

Matsubayashi et al. "Mass fragmentographic determination of lofepramine . . ." CA 88:31799 1978.
Kimura et al. "Metabolism of an antidepressant, Lofepramine . . ." CA 90:179852 1979.

Jolles et al. "Drug design: fact of fantasy" Academic Press, pp. 47–49, 57–58 1984.

Bundgaard et al. "A novel solution–stable water soluble prodrug . . ." J. Med. Chem. v. 32, pp. 2503–2507 1989.

*Primary Examiner*—Ceila Chang
*Attorney, Agent, or Firm*—Birch, Stewart, Kolasch & Birch, LLP

[57] ABSTRACT

The invention relates to new N-benzoylmethyl-piperidines of the general formula (I):

wherein X is a halogen atom, as well as their pharmaceutically acceptable addition salts. The compounds are potentially useful to treat depressions.

10 Claims, No Drawings

N-BENZOYLMETHYL-PIPERIDINES

This application is a 371 of PCT/EP95/01007 filed Mar. 17, 1995.

The present invention relates to new N-benzoylmethyl-piperidines of the general formula (I):

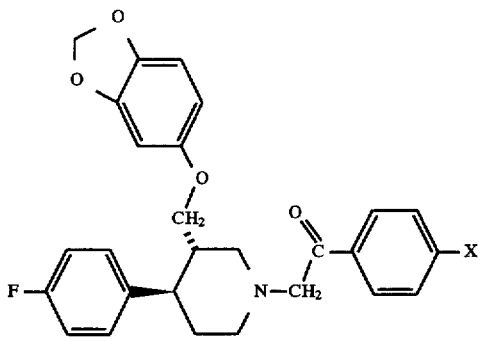

wherein X is a halogen atom, as well as their pharmaceutically acceptable addition salts.

In the compounds of the general formula (I), the halogen represented by X is preferably chlorine or fluorine, but more preferably fluorine. Among the pharmaceutically acceptable salts, hydrochloride is preferred.

The compounds of the present invention are prepared by alkylation of (−)-trans-4-(p-fluorophenyl)-3-[[3,4-(methylenedioxy)phenoxy]methyl]-piperidine, antidepressant known as paroxetine, having the structural formula (II):

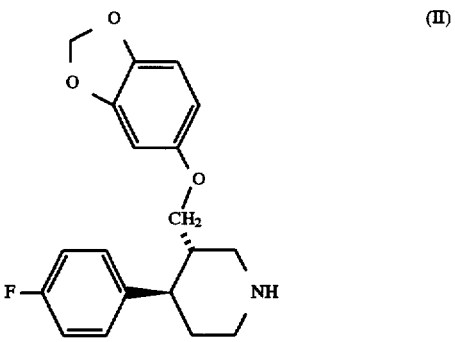

with p-halo-phenacyl halide of the general formula (III):

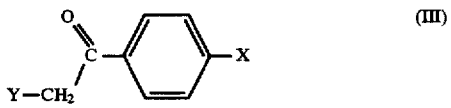

wherein X is defined as in (I) and Y may be either chlorine or bromine. This alkylation occurs advantageously in an anhydrous alcohol medium and in the presence of a mineral base that facilitates the uptake reaction of the formed hydracid. Among solvents, low molecular weight alkanols, such as methanol or ethanol, are preferred, and among bases, alkali metal carbonates or hydrogen carbonates, such as sodium hydrogen carbonate, are preferred. As the reaction is enhanced by heat release, it is advisable to perform it at the boiling temperature of the mixture.

British Patent No. 1.422.263 describes the preparation of the piperidine of the formula (II) as well as its antidepressant properties on the basis of its ability to inhibit 5-hydroxytryptamine (5HT) reuptake selectively.

Applicants have found out that the compounds of the present invention are also able to inhibit 5-hydroxytryptamine reuptake in the same manner as the compound they derive from. However, these compounds advantageously exhibit lower toxicity signs while the selective inhibition degree of 5-hydroxytryptamine reuptake is at least the one of paroxetine. The results on the reuptake inhibition of 5-hydroxytryptamine (5HT) and dopamine (DA) in rat brain synaptosomes, which are expressed as molar concentrations, are shown in Table 1. This test was performed according to the method described by Ferris RM et al ("Pharmacol.Drug Dev.Res.", 1, 21–35, 1981) and revealed that the compound of Ex. 1 is at least as selective as paroxetine, while the compound of Ex. 2 is seven times more selective.

TABLE 1

| | $IC_{50}$ (M) | | | |
| Compound | 5HT (cortex) | DA (striatum) | 5HT/DA Selectivity | Relative Selectivity* |
| --- | --- | --- | --- | --- |
| Example 1 | $2.11 \times 10^{-8}$ | $>1 \times 10^{-5}$ | >474 | >1.06 |
| Example 2 | $6.85 \times 10^{-9}$ | $2.22 \times 10^{-5}$ | 3241 | 7.25 |
| Paroxetine | $2.46 \times 10^{-9}$ | $1.10 \times 10^{-6}$ | 447 | 1 |

*Relative selectivity versus paroxetine.

The lower toxicity of the compounds of this invention with regard to paroxetine has been made evident by Irwin test ("Science", 136, 123, 1962) in mice administered orally with test substances. Under test conditions, paroxetine at the dose of 400 mg/kg caused convulsions, mydriasis and Straub tail. In contrast, the compound of Ex. 1 at the dose of 600 mg/kg did not show any sign of toxicity, while in the compound of Ex. 2 merely the onset of manifestations of hyperactivity was observed at the dose of 800 mg/kg. These findings are most important, since the safety range of the compounds of this invention makes them be highly useful for their clinical application.

EXAMPLE 1

(−)-Trans-N-p-fluorobenzoylmethyl-4-(p-fluorophenyl)-3-[[3,4-(methylenedioxy)phenoxy]methyl]-piperidine hydrochloride (−)-Trans-4-(p-fluorophenyl)-3-[[3,4-(methylenedioxy)phenoxy]methyl]-piperidine hydrochloride (7.32 g, 0.02 mole) was dissolved in absolute ethyl alcohol (100 ml). Then, $NaHCO_3$ (6.38 g, 0.076 mole) and 2-chloro-4'-fluoroacetophenone (4.49 g, 0.026 mole) were added and refluxed for 3 hours. The solution was cooled, the inorganic salts were filtered, the solid was washed with small volumes of ethanol, and the liquid phase was evaporated till all methanol was removed to afford a resin. This latter material was then dissolved in chloroform (150 ml), filtered through 70–230 mesh ASTM silica gel 60 (150 g), and eluted with a gradient of $Cl_3CH$:MeOH. The fractions showing by TLC the presence of pure product were combined, and the solvent was evaporated. The resin thus obtained was dissolved in ethyl ether (150 ml), the solid formed was filtered, and the liquid was treated under vigorous stirring with hydrochloric acid 5M in ethyl ether (4 ml). The solid crystallized was filtered, washed with ethyl ether and recrystallized in acetone-ethyl ether to yield 5.6 g (57%).

IR (KBr): 3440, 2950, 1700, 1600, 1510, 1490, 1230, 1180 $cm^{-1}$.

$^1$H-NMR (DMSO): The signals recorded and their interpretation are as follows:

| δ | multiplicity | assignment |
|---|---|---|
| 11.10 | s | 1H NH+ |
| 8.10 | d | 2H 1', 3' |
| 7.48 | dd | 2H 2', 4' |
| 7.30 | dd | 2H 1''', 4''' |
| 7.20 | dd | 2H 2''', 3''' |
| 6.70 | d | 1H 2" |
| 6.50 | d | 1H 3" |
| 6.20 | dd | 1H 1" |
| 5.95 | s | 2H —O—CH$_2$—O— |
| 5.25 | s | 2H —N—CH$_2$— |
| 3.2–4.0 | m | 5H —O—CH$_2$—, 2eq, 6eq, 6ax |
| 2.90 | m | 2H 2ax, 4 |
| 2.45 | m | 2H, 3, 5ax |
| 1.95 | d | 1H 5eq |

Elemental analysis for $C_{27}H_{25}F_2NO_4 \cdot HCl$: (found) C 62.37 H 4.94 N 2.71 Cl⁻ 6.69; (calcd.) C 64.61 H 5.22 N 2.79 Cl⁻ 7.06. Melting point: 216°–219° C. (d). $[\alpha]_D$ at 0.5% (ethanol): −51°. 1 basic group: 98.4.

EXAMPLE 2

(−)-Trans-N-p-chlorobenzoylmethyl-4-(p-fluorophenyl)-3-[[3,4-(methylenedioxy)phenoxy]methyl]-piperidine hydrochloride (−)-Trans-4-(p-fluorophenyl)-3-[[3,4-(methylenedioxy)phenoxy]methyl]-piperidine hydrochloride (4.3 g, 0.0118 mole) was dissolved in absolute ethanol (100 ml). Then, NaHCO$_3$ (3.5 g, 0.0413 mole) and 2-bromo-4'-chloroacetophenone (3.32 g, 0.0142 mole) were added and refluxed for 3 hours. The inorganic salts were filtered and washed with ethanol, and the liquid phase was evaporated till all methanol was removed to afford a resin. This latter material was then dissolved in chloroform (250 ml), filtered through 70–230 mesh ASTM silica gel 60 (150 g), and eluted with a gradient of Cl$_3$CH:MeOH. The fractions showing by TLC the presence of pure product were combined and evaporated to dryness. The resin thus obtained was dissolved in ethyl ether (150 ml), the solid residues were filtered, and to the filtrates hydrochloric acid 5M in ethyl ether (5 ml) was added under vigorous stirring. The solid precipitated was recrystallized in acetone-ethyl ether to yield 3.6 g (59%).

IR (KBr): 3430, 2950, 1695, 1595, 1510, 1490, 1235, 1185 cm⁻¹.

¹H-NMR (DMSO): The signals recorded and their interpretation are as follows:

| δ | multiplicity | assignment |
|---|---|---|
| 8.05 | d | 2H 1', 3' |
| 7.75 | d | 2H 2', 4' |
| 7.30 | dd | 2H 1''', 4''' |
| 7.19 | dd | 2H 2''', 3''' |
| 6.75 | d | 1H 2" |
| 6.50 | d | 1H 3" |
| 6.20 | dd | 1H 1" |
| 5.93 | s | 2H —O—CH$_2$—O— |
| 5.20 | s | 2H —N—CH$_2$— |
| 3.2–3.9 | m | 5H —O—CH$_2$—, 2eq, 6eq, 6ax |
| 2.90 | m | 2H 2ax, 4 |
| 2.35 | m | 2H 5ax, 3 |
| 1.98 | d | 1H 5eq |

Elemental analysis for $C_{27}H_{25}ClFNO_4 \cdot HCl$: (found) C 61.92 H 5.02 N 2.57 Cl 13.36 Cl⁻ 7.1; (calcd.) C 62.56 H 5.06 N 2.70 Cl 13.68 Cl⁻ 6.84. Melting point: 203°–209° C. (d). $[\alpha]_D$ at 0.5% (ethanol): −40°. 1 basic group: 97.8%.

EXAMPLE 3

Formulation of 10 mg Tablets

Composition per 1 tablet:

(−)-Trans-N-p-fluorobenzoylmethyl-4-(p-fluorophenyl)-3-[[3,4-(methylenedioxy)phenoxy]methyl]-piperidine hydrochloride . . . 10.0 mg Corn starch . . . 43.2 mg Talc . . . 6.0 mg Hydrogenated castor oil . . . 2.0 mg Lactose to volume . . . 200.0 mg

EXAMPLE 4

Formulation of 50 mg Tablets

Composition per 1 tablet:

(−)-Trans-N-p-fluorobenzoylmethyl-4-(p-fluorophenyl)-3-[[3,4-(methylenedioxy)phenoxy]methyl]-piperidine hydrochloride . . . 50.0 mg Corn starch . . . 86.4 mg Talc . . . 12.0 mg Hydrogenated castor oil . . . 4.0 mg Lactose to volume . . . 400.0 mg

We claim:

1. A N-Benzoylmethyl-piperidine of formula (I):

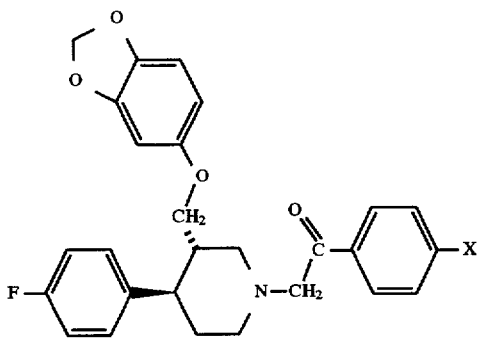

wherein X is a halogen atom or a pharmaceutically acceptable addition salt thereof.

2. A N-Benzoylmethyl-piperidine according to claim 1, wherein X is fluorine or chlorine.

3. A N-Benzoylmethyl-piperidine addition salt according to claim 1 which is in the form of a pharmaceutically acceptable hydrochloride addition salt.

4. A method for treating depression which comprises administering an effective amount of at least one compound of formula (I) or a pharmaceutically acceptable additional salt according to claim 1.

5. A pharmaceutical composition comprising at least one compound according to claim 1, together with pharmaceutically acceptable carriers and/or adjuvants.

6. A process for preparing a compound of formula I according to claim 1, which comprises alkylating a compound of formula II

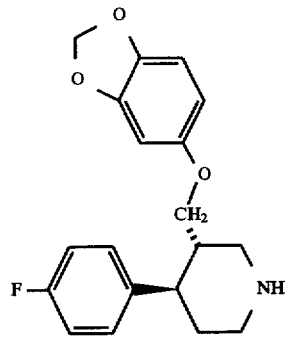

with a p-halophenacyl compound of the formula III:

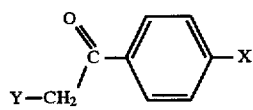

wherein Y is chlorine or bromine, and X is as defined in claim 1, and, optionally converting the compound of formula I in free base form into an acid addition salt thereof.

7. A N-Benzoylmethyl-piperidine according to claim 2 which is in the form of a pharmaceutically acceptable hydrochloride addition salt.

8. A pharmaceutical composition comprising at least one compound according to claim 2, together with pharmaceutically acceptable carriers and/or adjuvants.

9. The process according to claim 6, wherein X is fluorine or chlorine.

10. The process according to claim 9, wherein the N-Benzoylmethyl-piperidine is in the form of a pharmaceutically acceptable hydrochloride salt.

* * * * *